US009924879B2

United States Patent
Van Den Heuvel et al.

(10) Patent No.: US 9,924,879 B2
(45) Date of Patent: Mar. 27, 2018

(54) FEVER DETECTION APPARATUS

(75) Inventors: Teun Van Den Heuvel, Waalre (NL); Jens Muehlsteff, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 642 days.

(21) Appl. No.: 14/117,633

(22) PCT Filed: May 21, 2012

(86) PCT No.: PCT/IB2012/052529
§ 371 (c)(1),
(2), (4) Date: Nov. 14, 2013

(87) PCT Pub. No.: WO2012/160500
PCT Pub. Date: Nov. 29, 2012

(65) Prior Publication Data
US 2014/0088443 A1 Mar. 27, 2014

(30) Foreign Application Priority Data
May 26, 2011 (EP) .................................... 11167745

(51) Int. Cl.
*A61B 5/0205* (2006.01)
*A61B 5/01* (2006.01)
(Continued)

(52) U.S. Cl.
CPC ............ *A61B 5/02055* (2013.01); *A61B 5/01* (2013.01); *A61B 5/026* (2013.01);
(Continued)

(58) Field of Classification Search
None
See application file for complete search history.

(56) References Cited

U.S. PATENT DOCUMENTS 4,621,643 A * 11/1986 New, Jr. ............. A61B 5/14552
250/252.1
5,844,862 A 12/1998 Cocatre-Zilgien
(Continued)

FOREIGN PATENT DOCUMENTS

CN 102046085 A 5/2011
JP H0871046 A 3/1996
(Continued)

OTHER PUBLICATIONS

Thompson, M., et al. "Deriving temperature and age appropriate heart rate centiles for children with acute infections." (2009) Archives of disease in childhood 94.5: 361-365.*
(Continued)

*Primary Examiner* — Jacqueline Cheng
*Assistant Examiner* — Jairo Portillo

(57) ABSTRACT

The invention relates to a fever detection apparatus for detecting fever of a living being. A heart rate providing unit (3) provides a heart rate value and a peripheral physiological value providing unit (3) provides a peripheral physiological value, wherein a heart rate characteristics determination unit (4) determines heart rate characteristics from the heart rate value and a peripheral characteristics determination unit (5) determines peripheral characteristics from the peripheral physiological value. A fever detection unit (6) detects fever depending on the heart rate characteristics and the peripheral characteristics. Since the heart rate characteristics and the peripheral characteristics are influenced by fever, the fever detection apparatus can be used to reliably and preferentially unobtrusively detect fever.

19 Claims, 3 Drawing Sheets

(51) Int. Cl.
*A61B 5/026* (2006.01)
*A61B 5/00* (2006.01)
*A61B 5/024* (2006.01)

(52) U.S. Cl.
CPC ........ *A61B 5/02438* (2013.01); *A61B 5/6824* (2013.01); *A61B 5/7275* (2013.01); *A61B 5/7282* (2013.01); *A61B 5/0008* (2013.01); *A61B 5/024* (2013.01); *A61B 5/02416* (2013.01)

(56) References Cited

U.S. PATENT DOCUMENTS

| | | | | |
|---|---|---|---|---|
| 6,312,391 | B1* | 11/2001 | Ramadhyani | A61B 5/015 600/549 |
| 6,356,774 | B1* | 3/2002 | Bernstein | A61B 5/14552 600/322 |
| 7,043,287 | B1* | 5/2006 | Khalil | A61B 5/0059 600/310 |
| 2001/0044588 | A1 | 11/2001 | Mault | |
| 2002/0077766 | A1 | 6/2002 | Mault | |
| 2002/0114375 | A1* | 8/2002 | Pompei | G01J 5/0022 374/133 |
| 2002/0156386 | A1* | 10/2002 | Dardik | A61B 5/0002 600/520 |
| 2003/0045908 | A1* | 3/2003 | Condie | A61B 5/0472 607/9 |
| 2004/0260161 | A1* | 12/2004 | Melker | A61B 5/0873 600/340 |
| 2005/0177064 | A1 | 8/2005 | Rubinstein | |
| 2005/0245839 | A1 | 11/2005 | Stivoric et al. | |
| 2005/0276309 | A1* | 12/2005 | Koch | A61B 5/6831 374/208 |
| 2006/0142802 | A1* | 6/2006 | Armstrong | A61B 5/01 607/2 |
| 2007/0161921 | A1* | 7/2007 | Rausch | G06F 19/3406 600/549 |
| 2008/0167535 | A1* | 7/2008 | Stivoric | G01R 29/0814 600/301 |
| 2008/0221419 | A1 | 9/2008 | Furman | |
| 2008/0275349 | A1* | 11/2008 | Halperin | A61B 5/0205 600/484 |
| 2009/0105560 | A1 | 4/2009 | Solomon | |
| 2010/0022909 | A1 | 1/2010 | Padiy | |
| 2014/0088443 | A1 | 3/2014 | Heuvel et al. | |

FOREIGN PATENT DOCUMENTS

| | | | |
|---|---|---|---|
| JP | 2005034391 A | 2/2005 | |
| JP | 2007229080 A | 9/2007 | |
| JP | 2010148718 A | 7/2010 | |
| JP | 2010194133 A | 9/2010 | |
| JP | 2011036416 A | 2/2011 | |
| KR | 20100005880 A | 1/2010 | |
| TW | 201103496 | * 2/2011 | ............... A61B 5/02 |

OTHER PUBLICATIONS

Nakamura, Kazuhiro. "Central circuitries for body temperature regulation and fever." (2011) American Journal of Physiology-Regulatory, Integrative and Comparative Physiology 301.5: R1207-R1228.*

Cabanac, Michel, and Seika Aizawa. "Fever and tachycardia in a bird (Gallus domesticus) after simple handling." (2000) Physiology & behavior 69.4: 541-545.*

* cited by examiner

FEVER DETECTION APPARATUS

FIELD OF THE INVENTION

The invention relates to a fever detection apparatus, a fever detection method and a fever detection computer program for detecting fever of a living being.

BACKGROUND OF THE INVENTION

US 2005/0276309 A1 discloses a device for measuring a body core temperature of a person. The device comprises a means, which can be firmly wrapped around an upper part of the body of the person, wherein to this means a double temperature sensor is attached such that it is pressed elastically onto the area of the sternum of the person.

US 2001/0044588 A1 discloses a monitor system for allowing a person to remotely monitor a temperature of a subject. The monitor system comprises a sensor system, a computing device and a software application program. The sensor system includes a transducer, which is adapted to provide a transducer signal correlated with the temperature, and a transmitter, which is adapted to receive the transducer signal and to transmit a wireless signal carrying data correlated with the temperature. The computing device includes a receiver adapted to receive the wireless signal transmitted by the sensor system and to provide a receiver signal. The software application program is adapted to determine a temperature value from the receiver signal, to store the temperature value in a memory and to show a chart of a plurality of temperature values on a display, when the software application program runs on the computing device.

US 2008/0221419 A1 discloses a system for monitoring a health condition. The system comprises a monitoring device with an optical sensor for sensing a relative position of a vessel, a Doppler sensor for sensing a velocity of a fluid flowing in the vessel and a computing device for operating the optical sensor and the Doppler sensor to obtain health parameter values like the oxygen saturation of the blood or the heart rate.

US 2009/0105560 A1 discloses a computerized system for scheduling at least one daily activity of a user. One or more sensors are attached to the body of the user, which monitor one or more physiological parameters preferentially including the skin temperature and the heart rate, thereby producing physiological data representing the one or more physiological parameters during a time period. A processing unit is programmed for scheduling activities based on the physiological data and based on previously stored values. The scheduled activities can include eating of a meal, exercise or rest of the user. If, in an example, the scheduled daily activity is eating of a meal, the processing unit can be programmed to recommend to the user to eat the meal during a portion of the time period, when the skin temperature is rising or when the heart rate is falling.

US 2005/0177064 A1 discloses a fever alarm system comprising a body temperature measurement device which includes a unit that continuously measures the body temperature and transmits the measurement through a radio frequency transmitter to a display unit. The body temperature is measured by measuring the skin temperature and an ambient room temperature and by determining the body temperature depending on the measured skin temperature and the measured ambient room temperature. The display unit includes a radio frequency receiver, an adjustable threshold alarm circuit and a display that shows the body temperature. The adjustable threshold alarm circuit is adapted to turn on an alarm whenever the measured body temperature rises above a defined threshold. However, the body temperature, which is determined as described above, may be increased, even if fever is not present, and fever may be present, even if the determined body temperature is not increased, thereby reducing the reliability of detecting fever.

SUMMARY OF THE INVENTION

It is an object of the present invention to provide a fever detection apparatus, a fever detection method and a fever detection computer program for detecting fever of a living being, wherein the reliability of detecting fever can be improved.

In a first aspect of the present invention a fever detection apparatus for detecting fever of a living being is presented, wherein the fever detection apparatus comprises:

a heart rate providing unit for providing a heart rate value being indicative of the heart rate of the living being measured over time, a peripheral physiological value providing unit for providing a peripheral physiological value being indicative of a peripheral physiological property of the living being measured over time, a heart rate characteristics determination unit for determining heart rate characteristics from the heart rate value measured over time, a peripheral characteristics determination unit for determining peripheral characteristics from the peripheral physiological value measured over time, a fever detection unit for detecting fever depending on the heart rate characteristics and the peripheral characteristics.

Fever is characterized by an increased neural set point of the core body temperature control. At the onset of fever, the set point is higher than the initial core body temperature. The body therefore acts to increase the core body temperature by increasing heat production and preventing heat loss to its surroundings. Physiological mechanisms for the regulation of body heat production relate to metabolism, which in turn is strongly related to heart rate. A major physiological mechanism for the regulation of body heat loss involves regulation of the peripheral physiological properties like the skin temperature and/or the amount of superficial and peripheral blood perfusion. The heart rate characteristics determined from the heart rate measured over time and the peripheral characteristics determined from the peripheral physiological value measured over time are therefore influenced by fever and can therefore be combined and used for improving the reliability of detecting fever.

The heart rate providing unit can be a heart rate measuring unit for measuring the heart rate values, or a storing unit for storing already measured heart rate values, wherein the heart values can be retrieved from the storing unit for retrieving the same. Moreover, the heart rate providing unit can also be a receiving unit for receiving the heart rate values from, for example, a corresponding measuring unit and for providing the received heart rate values. Similarly, also the peripheral physiological value providing unit or optional further providing units for providing further properties can be, for example, a measuring unit, a storing unit or a receiving unit.

The heart rate characteristics and the peripheral characteristics can be temporal characteristics, in particular, temporal patterns.

The living being is preferentially a person or a warm-blooded animal.

The peripheral physiological value is indicative of a physiological property of the periphery of the living being, in particular, of the skin and/or an extremity like a finger of the living being. The heart rate value is, for example, the pulse rate. However, the heart rate value can also be any other value being indicative of the heart rate.

In a preferred embodiment, the heart rate and the peripheral physiological property are measured unobtrusively, i.e. the fever detection apparatus is preferentially adapted to unobtrusively detect fever with improved reliability.

It is preferred that the fever detection unit is adapted to apply predefined fever detection rules to the heart rate characteristics and the peripheral characteristics. It is also preferred that a) the heart rate characteristics and the peripheral characteristics are determined such and b) the fever detection rules are predefined such that fever is detected, if the heart rate value increases and the peripheral physiological value decreases in a same time interval. In particular, the fever detection unit is adapted to detect fever, if the increase of the heart rate value and the decrease of the peripheral physiological value are measured simultaneously.

The fever detection unit can be adapted to determine a heart rate gradient from the heart rate value measured over time as heart rate characteristics and a peripheral gradient from the peripheral physiological value measured over time as peripheral characteristics. The gradient is preferentially determined by determining how the amplitude of the respective value has changed between two different points in time. This allows determining and quantifying changes in the heart rate and in the peripheral physiological value in a relatively simple way.

In an embodiment, the fever detection rules are predefined such that fever is detected, if the heart rate gradient is positive indicating a heart rate increase and the peripheral gradient is negative indicating a decrease of the peripheral physiological property within a same time interval. In particular, the fever detection rules are predefined such that fever is detected, if simultaneously the peripheral gradient is negative indicating a decrease of the peripheral physiological value and the heart rate gradient is positive indicating a heart rate increase within a same time interval. Moreover, the fever detection rules can be predefined such that fever is detected, if additionally the absolute peripheral gradient is larger than a peripheral threshold and the absolute heart rate gradient is larger than a heart rate threshold. The peripheral and heart rate thresholds are, for example, predefined constant thresholds or adaptive threshold, which may depend on a property of the living being like the body posture. This allows detecting fever only if a substantial decrease in the peripheral physiological value, for example, in skin temperature and/or in peripheral perfusion, is detected together with a substantial increase in heart rate. This further improves the reliability of detecting fever.

In a further embodiment, the heart rate providing unit is adapted to provide an initial heart rate value and an actual heart rate value, wherein the peripheral physiological value providing unit is adapted to provide an initial physiological value and an actual physiological value, wherein the fever detection unit is adapted to determine a heart rate change based on the provided initial and actual heart rates as heart rate characteristics and a peripheral change based on the provided initial and actual physiological values as peripheral characteristics, and wherein the fever detection rules are predefined such that fever is detected, if the heart rate change indicates an increase of the heart rate and the peripheral change indicates a decrease of the peripheral physiological value in a same time interval. The initial values can be regarded as basal values, which can be measured at the beginning of a monitoring process and/or after a condition of the living being like the body posture has been changed. The heart rate change and the peripheral change can be, for example, differences or ratios. If, for instance, at the beginning of a monitoring process it has been determined by, for example, a nurse or a caregiver that the living being does not have fever, the fever detection apparatus can continuously determine the heart rate change and the peripheral change and detect fever depending on the determined heart rate and peripheral changes. Also in this embodiment, the fever detection rules can be predefined such that fever is detected, if additionally the absolute heart rate change and the absolute peripheral change are larger than corresponding peripheral and heart rate thresholds. These thresholds can be predefined constant thresholds or adaptive thresholds, which depend, for instance, on the initial heart rate value and the initial peripheral value.

It is further preferred that the fever detection unit is adapted to apply predefined fever probability rules to the peripheral characteristics and the heart rate characteristics for determining a fever property value being indicative of the probability of having fever. Thus, the fever detection unit cannot only be adapted to perform a binary decision whether fever is present or not, but the fever detection unit can also be adapted to determine the probability of having fever. For example, the fever probability rules can provide assignments between a) different fever probability values and b) peripheral characteristics and heart rate characteristics. The fever probability rules, i.e., for example, the assignments, can be determined by determining the percentage of situations in which the respective characteristics have been found to relate to fever. The probability values can be defined such that a probability of 0% relates to a condition, in which fever is surely not present, and a probability value of 100% corresponds to a condition, in which the living being surely has fever. The probability values between 0% and 100% can be defined with respect to any convenient scale. The fever probability rules can also include the fever detection rules, i.e. if fever probability rules are used, it can be defined that fever is detected if the probability value is larger than a probability threshold, in particular, if the probability value is 100%. Further, separate fever detection rules are then not necessarily needed. Also the probability threshold can be a predefined constant threshold or an adaptive threshold, which may depend on a property of the living being like the body posture.

In a preferred embodiment, the fever detection unit is further adapted to detect recovery from fever depending on the heart rate characteristics and the peripheral characteristics. The fever detection unit can be adapted to apply predefined fever recovery rules to the peripheral characteristics and the heart rate characteristics for detecting recovery from fever. In particular, the fever detection unit can be adapted to apply predefined fever recovery rules to the peripheral characteristics and the heart rate characteristics for detecting recovery from fever, wherein a) the peripheral characteristics and the heart rate characteristics are determined such and b) the fever recovery rules are predefined such that recovery from fever is detected, if the peripheral physiological value increases and the heart rate decreases in a same time interval. Thus, if fever has been detected, the recovery from fever can also be detected by the fever detection unit.

The fever detection apparatus can further comprise a property measurement unit for measuring a further property of the living being or a property of the surrounding of the living being, wherein the fever detection unit is adapted to detect fever depending on the peripheral physiological value, the heart rate value and the property measured by the property measurement unit. In an embodiment, the property measurement unit is adapted to measure at least one of: ambient temperature, respiratory rate, physical activity type, physical activity level, body posture, body movement. The further property measured by the property measurement unit can also be used to determine the fever probability value and/or to detect a recovery from fever. Moreover, the above mentioned rules can be adapted to be also applied to the further property, in order to further improve the reliability of detecting fever, recovery from fever and/or the reliability of determining the fever probability. For example, thresholds used by the rules can depend on the measured further property. In an embodiment, the above mentioned peripheral and/or heart rate thresholds can depend on the posture of the living being.

In an embodiment, the property measurement unit measures the movement and/or relative height of the part of the living being at which the peripheral physiological property is measured. For example, the movement and/or relative height of the hand or arm can be measured, and the fever detection unit can be adapted such that a fever detection procedure is only performed, if the movement is below a predefined threshold and/or the relative height is within a predefined acceptance window. Furthermore, the fever detection unit may be adapted to determine whether fever is present or not depending on a perfusion measurement, only if the movement is below the predefined threshold and/or the relative height is within the predefined acceptance window and optionally only after a predefined time interval after the movement was above the predefined threshold and/or the relative height was outside of the predefined acceptance window. The movement can be measured by using, for example, an accelerometer. The measurement of the relative height can be performed by using, for example, a barometer. The relative height can be determined with respect to a reference height which can be a height measured at the beginning of the monitoring process. For example, the relative height can be the ratio of the actual height to the reference height. The property measurement unit can be adapted to automatically measure the reference height, when a fever monitoring process starts, or the property measurement unit can be adapted to allow a user like a nurse or care giver to trigger a determination of the reference height, in particular, if the person is in a predefined posture, for which the fever detection apparatus may be calibrated.

The fever detection apparatus preferentially further comprises an output unit for outputting a signal, if fever has been detected.

It is also preferred that the heart rate providing unit is a heart rate measuring unit and the peripheral physiological value providing unit is a peripheral measuring unit, wherein the heart rate measuring unit and peripheral measuring unit are combined in a pulse oximeter for measuring a pulse rate as the heart rate value and a perfusion value as the peripheral physiological value. This allows measuring the heart rate value and the peripheral physiological value relatively easily with a single measurement device, which can be attached to the living being and which may further be used to serve other functions like blood oxygenation monitoring.

In a further aspect of the present invention a fever detection method for detecting fever of a living being is presented, wherein the fever detection method comprises:
providing a heart rate value being indicative of the heart rate of the living being measured over time by a heart rate measuring unit,
providing a peripheral physiological value being indicative of a peripheral physiological property of the living being measured over time by a peripheral measuring unit,
determining heart rate characteristics from the heart rate value measured over time by a heart rate characteristics determination unit,
determining peripheral characteristics from the peripheral physiological value measured over time by a peripheral characteristics determination unit,
detecting fever depending on the heart rate characteristics and the peripheral characteristics by a fever detection unit.

These and other aspects of the invention will be apparent from and elucidated with reference to the embodiments described hereinafter.

DETAILED DESCRIPTION OF EMBODIMENTS

Figure 1:
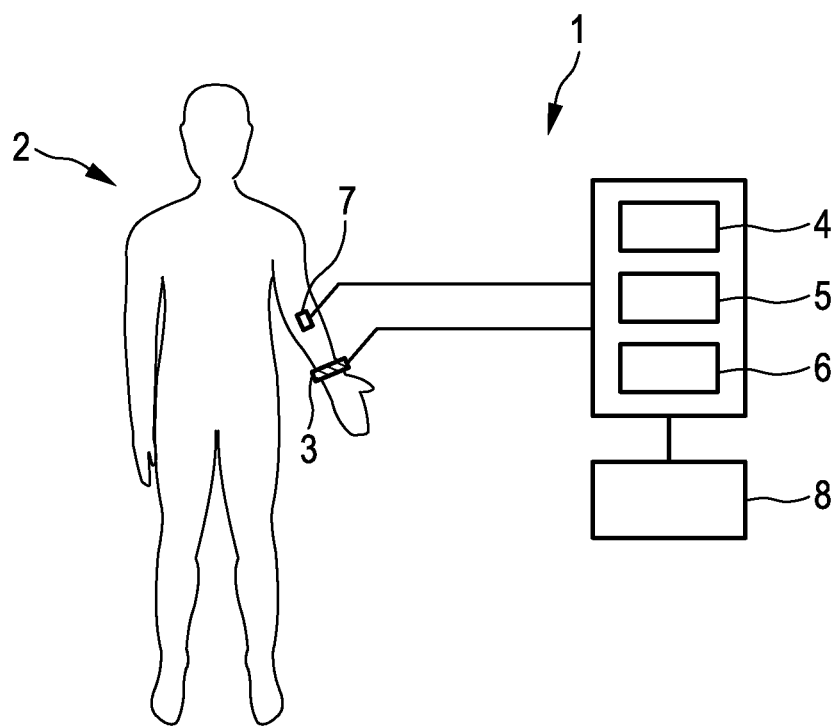
FIG. 1 shows schematically and exemplarily an embodiment of a fever detection apparatus for detecting fever of a living being.

FIG. 1 shows schematically and exemplarily an embodiment of a fever detection apparatus for detecting fever of a living being. The living being is, in this embodiment, a person 2. However, in another embodiment the living being can also be an animal. The fever detection apparatus 1 comprises a combined measuring unit 3 including a heart rate measuring unit for measuring a heart rate value being indicative of the heart rate of the person 2 over time and a peripheral measuring unit for measuring a peripheral physiological value being indicative of a peripheral physiological property of the person 2 over time. In particular, the combined measuring unit 3 is adapted to measure the pulse rate as heart rate value and to measure at least one of a skin temperature value being indicative of a skin temperature of the person 2 and a peripheral perfusion value being indicative of the blood perfusion in the periphery of the person 2 as the peripheral physiological value. In this embodiment, the combined measuring unit 3 is attached to an arm of the person 2 and measures the pulse rate and at least one of the skin temperature and the superficial blood perfusion as the peripheral physiological value. For measuring the pulse rate and the superficial blood perfusion a pulse oximeter is preferentially used as the combined measuring unit 3.

The fever detection apparatus 1 further comprises a heart rate characteristics determination unit 4 for determining heart rate characteristics from the heart rate measured over time and a peripheral characteristics determination unit 5 for determining peripheral characteristics from the peripheral physiological value measured over time. The heart rate characteristics and the peripheral characteristics can be temporal characteristics defining a temporal pattern. For example, the heart rate characteristics and the peripheral characteristics describe how the heart rate or the peripheral physiological value increase or decrease in a certain time interval.

The fever detection apparatus 1 further comprises a fever detection unit 6 for detecting fever depending on the heart rate characteristics and the peripheral characteristics. In particular, the fever detection unit 6 is adapted to apply predefined fever detection rules to the heart rate characteristics and the peripheral characteristics, wherein a) the heart rate characteristics and the peripheral characteristics are determined such and b) the fever detection rules are predefined such that fever is detected, if the heart rate value increases and the peripheral physiological value decreases in a same time interval. The fever detection unit 6 is preferentially adapted to detect fever, if a substantial increase of the heart rate value and a substantial decrease of the peripheral physiological value are measured simultaneously. Such a situation is schematically and exemplarily shown in FIG. 2.

Figure 2:
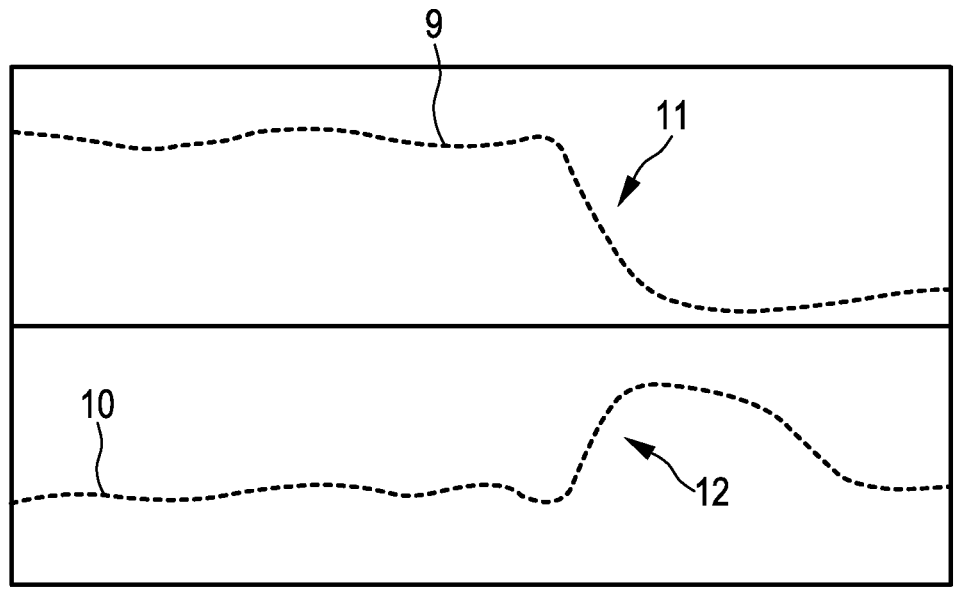
FIG. 2 shows a heart rate value and a peripheral physiological value measured over time in a situation, in which fever is detected.

FIG. 2 shows schematically and exemplarily the measured peripheral physiological value 9 depending on time and the measured heart rate value 10 depending on time. The heart rate value 10 shows an increase 12 and the peripheral physiological value shows a decrease 11 simultaneously, thereby allowing the fever detection unit 6 to detect fever.

Figure 3:
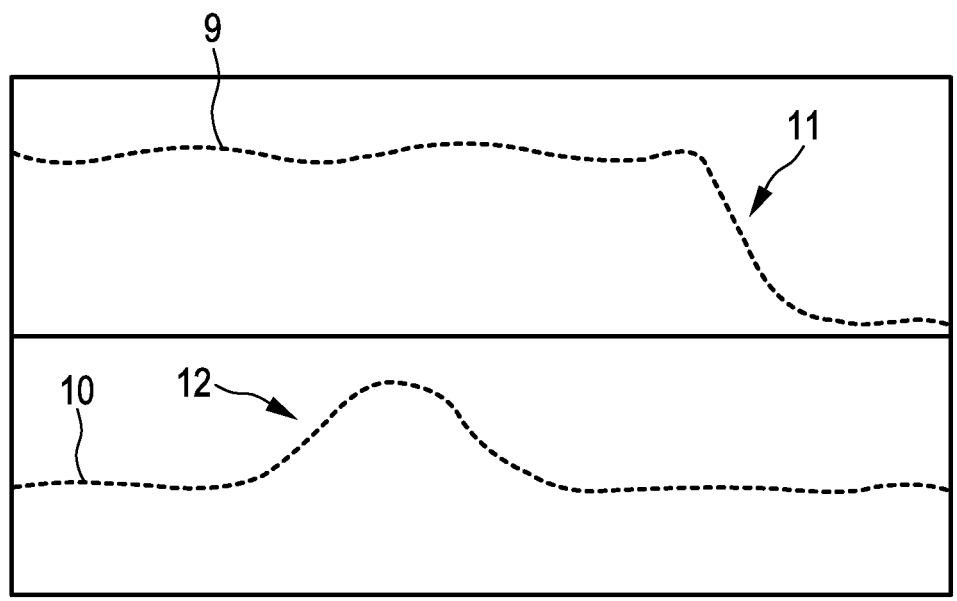
FIG. 3 shows schematically and exemplarily a heart rate value and a peripheral physiological value measured over time in a situation, in which fever is not detected.

FIG. 3 shows schematically and exemplarily other behaviors of the peripheral physiological value 9 and the heart rate value 10. Also in FIG. 3 the peripheral physiological value shows a decrease 11. However, at the time, at which the peripheral physiological value decreases, the heart rate value 10 does not increase. Moreover, also the heart rate value 10 shows an increase 12, but at the time, at which this increase 12 is present, there is no substantial decrease of the peripheral physiological value 9. Thus, in the situation shown in FIG. 3 the fever detection unit 6 will not detect fever.

In order to automatically detect fever, the fever detection unit can be adapted to, for example, determine a heart rate gradient from the heart rate value measured over time as heart rate characteristics and a peripheral gradient from the peripheral physiological value measured over time as peripheral characteristics, wherein the fever detection rules can be predefined such that fever is detected, if the heart rate gradient is positive indicating the heart rate increase and the peripheral gradient is negative indicating a decrease of the peripheral physiological property within a same time interval, in particular, simultaneously. In order to consider only substantial increases and decreases, the fever detection rules can be predefined such that fever is detected only, if additionally the absolute peripheral gradient is larger than a predefined peripheral threshold and the absolute heart rate gradient is larger than a predefined heart rate threshold.

The fever detection rules, for example, the temporal length of the same time interval, the peripheral threshold, the heart rate threshold, et cetera, can be determined by calibration measurements, wherein the heart rate characteristics and the peripheral characteristics are determined, while it is known whether the living being has fever or not, for example, by performing a parallel continuous measurement of the core body temperature using a rectal probe, and wherein the rules are predefined such that, if they are applied to the determined heart rate characteristics and peripheral characteristics, the known fever result, i.e. whether the living being has fever or not, is achieved.

The fever detection unit 6 can be further adapted to apply predefined fever probability rules to the peripheral characteristics and the heart rate characteristics for determining a fever property value being indicative of the probability of having fever. Thus, the fever detection unit can be adapted to not only provide a binary decision, according to which the living being has fever or not, but also a fever probability can be provided. Assignments between a) the peripheral characteristics and the heart rate characteristics and b) the probability values, which can define the fever probability rules, can be determined by determining the percentage of situations in which the respective characteristics have been found to relate to fever. The fever probability can therefore also be regarded as being an uncertainty measure to the fever detection.

The fever detection unit 6 is preferentially further adapted to detect recovery from fever depending on the heart rate characteristics and the peripheral characteristics. The fever detection unit 6 can be adapted to apply predefined fever recovery rules to the peripheral characteristics and the heart rate characteristics for detecting recovery from fever, wherein the predefined fever recovery rules are preferentially predefined such that recovery from fever is detected, if the peripheral physiological value substantially increases and the heart rate substantially decreases in the same time interval, in particular, simultaneously. Also this situation can be determined by, for example, determining corresponding gradients and comparing the absolute values of these gradients with corresponding thresholds.

The fever detection apparatus 1 can comprise a property measurement unit 7 for measuring a further property of the person 2 or a property of the surrounding of the person 2, wherein the fever detection unit 6 can be adapted to detect fever depending on the peripheral physiological value, the heart rate and the property measured by the property measurement unit. The measured property is, for example, the ambient temperature, the respiratory rate, the physical activity type, the physical activity level, the body posture, the body movement, the relative height of the combined measuring unit 3, et cetera. One or several property measurement units can be provided for measuring one or several of these properties. If one or several of these properties are also used for, for example, detecting fever, detecting a recovery from fever, and/or a probability of having fever, the corresponding rules are adapted such that they can be applied to the heart rate, the peripheral physiological value and the one or several further properties. For example, thresholds used by the rules can depend on the measured further property. In an embodiment, the above mentioned peripheral and/or heart rate thresholds can depend on the posture of the living being.

The fever detection apparatus 1 further comprises an output unit 8 for outputting a signal, if fever has been detected. For example, the output unit 8 can be a display showing a corresponding warning.

Figure 4:
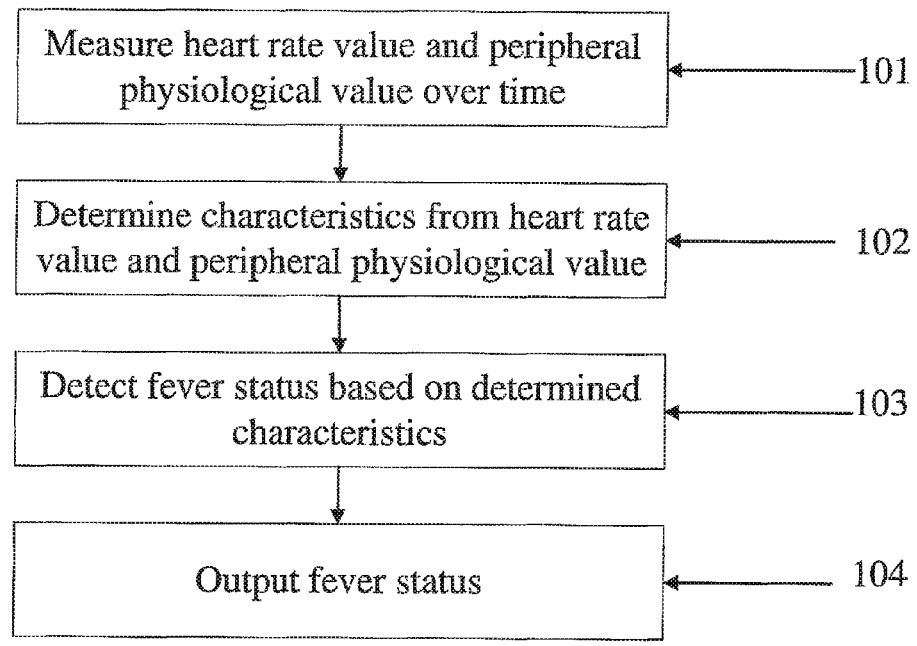
FIG. 4 shows a flowchart exemplarily illustrating an embodiment of a fever detection method for detecting fever of a living being.

FIG. 4 shows a flowchart exemplarily illustrating an embodiment of a fever detection method for detecting fever of a living being.

In step 101, the heart rate value being indicative of the heart rate of the living being and the peripheral physiological value being indicative of a peripheral physiological property of the living being are measured over time by the combined measuring unit 3 including the heart rate measuring unit and the peripheral measuring unit. For example, the skin temperature or the peripheral perfusion index is measured as the peripheral physiological value.

In step 102, heart rate characteristics are determined from the heart rate measured over time by the heart rate characteristics determination unit 4 and peripheral characteristics are determined from the peripheral physiological value measured over time by the peripheral characteristics determination unit 5. In step 103, the fever detection unit 6 detects whether the living being has fever or not depending on the heart rate characteristics and the peripheral characteristics. For example, fever is detected if the heart rate characteristics and the peripheral characteristics indicate that simultaneously a substantial increase of the heart rate and a substantial decrease of the peripheral physiological value are present. In step 104, the output unit 8 outputs whether fever has been detected or not.

The detection of fever is of major medical interest, since it may indicate infection. Moreover, very high fever poses a direct medical risk itself, as critical body functions tend to fail with high temperatures.

Fever is characterized by an increased neural set point for core body temperature control. At the onset of fever, the set point is higher than the initial core body temperature. The body therefore acts to increase the core body temperature by increasing heat production and preventing heat loss to its surroundings. These effects can subside somewhat as soon as the core body temperature matches the new, elevated neural set point. With recovery from fever, opposite effects occur: the set point is lowered so that the elevated core body temperature is experienced as too high, and the body acts to maximize heat loss and minimize heat production.

Physiological mechanisms for the regulation of body heat production relate to metabolism, which in turn is strongly related to the heart rate and, thus, the pulse rate. Therefore, the onset of fever can be associated with increased heart and pulse rates. A major physiological mechanism for the regulation of body heat loss involves regulation of the amount of superficial and peripheral blood perfusion: if heat is to be conserved, this perfusion may be minimized, most clearly so in the extremities. Therefore, the onset of fever can also be associated with a decreased peripheral perfusion index (PI), which is a measure of the degree of blood perfusion in, for example, a finger. Similarly, recovery from fever can be associated with an increased PI. The decreased perfusion can also lead to a decreased skin temperature such that a decreased skin temperature can also be associated with the onset of fever. Correspondingly, recovery from fever can be associated with an increased skin temperature.

The fever detection apparatus and method are therefore preferentially adapted to make use of combined temporal pattern detection in a) PI and/or skin temperature and b) pulse/heart rate, and with that optionally make use of pulse oximetry, for the purpose of automatic fever detection.

Common methods for fever detection involve observation or estimation of core body temperature. Since core body temperature cannot be observed directly from the outside of the body, these methods somehow have to compromise either reliability because of imperfection in estimation or patient comfort because of obtrusiveness or even invasiveness. Moreover, many of such methods require effort from a medically skilled person and are not feasible for continuous monitoring. The fever detection apparatus and method are preferentially adapted to overcome at least one of these disadvantages.

As already mentioned above, the fever detection apparatus and method are preferentially adapted to make use of combined information on a) PI and/or skin temperature and b) pulse rate, in particular, their changes over time, for the purpose of fever detection. Preferentially, temporal patterns in a) PI and/or skin temperature and b) pulse rate, in particular, their combinations, may be used for automatic detection of fever, i.e. the onset of fever, making observation or estimation of core temperature preferentially largely redundant.

The fever detection apparatus and method comprises at least some means to observe PI or skin temperature and some means to observe pulse rate/heart rate. A well known system to observe PI and pulse rate is a pulse oximeter which may be comprised by the fever detection apparatus. The observations over time, in particular, their changes, are recorded automatically. An automatic process is then provided to compare the records to preset criteria for the detection of onset of fever, which criteria include preferentially at least a) a substantial decrease in PI and/or skin temperature together with b) a substantial increase in pulse rate. Once it has been established that the detection criteria have been met, the detection of fever is communicated, for example, as a warning to a user or, more generally, as a message to an external system.

The fever detection apparatus and method are preferentially adapted such that, in a first processing level, both a) PI and/or skin temperature and b) pulse/heart rate are sampled. Preferentially, samples are subsequently fed into chronological lists of recent values. Based on these lists and on preset time and amplitude parameters, a) substantial decreases of PI or skin temperature and b) substantial increases of pulse/heart rate are detected. If both are detected simultaneously, detection of fever onset is constituted and communicated to an external system.

The sampling, recording, detection and messaging steps can be implemented on a dedicated electronic platform or on a personal computer, for example. For a wireless implementation, radio communication may be established to link any lower processing level to the subsequent level. Appropriate settings for parameters such as sampling rates and detection criteria like rates of increase and decrease, time windows, et cetera can be determined empirically.

Besides a) PI and/or skin temperature and b) pulse rate, also any, several or all of skin temperature, ambient temperature, respiratory rate, physical activity type, physical activity level and body posture may be observed and sampled to serve more accurate detection of fever onset, e.g. through improved sensitivity or targeted false alarm reduction. Typical fever related patterns in these properties, in particular, in combinations of these properties, can be determined empirically before application.

Especially in embodiments with PI observation on the hand or arm, it is preferred to also observe and consider the movement and/or relative height of the hand or arm, since these can affect PI substantially leading to false alarms if ignored. For example, PI observations may be ignored from the start until some time after arm movement as observed, for example, through an accelerometer.

In an above described embodiment, the fever detection apparatus and method are adapted to detect recovery from fever, if PI and/or skin temperature increases. However, additional measurements may also be employed to detect recovery from fever, as, for example, ambient temperature may drop because the patient typically feels hot and tries to establish a colder environment.

In an embodiment, at least parts of the fever detection apparatus like sensors, which may be combined with a battery, signal processing equipment and optional other components, may be integrated in a compact wireless device suited for attachment to the human body at a suitable location like a hand or an arm. Communication of fever detection messages may be realized through, for example, radio transmission, visual signs like blinking light-emitting diodes or an electronic display, or through sound via a loudspeaker.

The detection apparatus and method may be used in any situation where detection of fever is meaningful, especially in patient monitoring applications with medium to low risk levels like in general hospital wards and in home health care.

Although in the above descript embodiments the fever detection apparatus is adapted to detect fever depending on heart rate characteristics and peripheral characteristics in certain ways, the fever detection apparatus can also be adapted to detect fever depending on the heart rate characteristics and the peripheral characteristics in another way. For example, the heart rate providing unit can be adapted to provide an initial heart rate value and an actual heart rate value, and the peripheral physiological value providing unit can be adapted to provide an initial physiological value and an actual physiological value. The fever detection unit can then be adapted to determine a heart rate change based on the provided initial and actual heart rates as heart rate characteristics and a peripheral change based on the provided initial and actual physiological values as peripheral characteristics, wherein the fever detection rules can be predefined such that fever is detected, if the heart rate change indicates an increase of the heart rate and the peripheral change indicates a decrease of the peripheral physiological value in a same time interval. Thus, the fever detection apparatus can be adapted to detect fever depending on basal heart rate and peripheral values.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of heart rate characteristics and peripheral characteristics and the detection of fever depending on the heart rate characteristics and the peripheral characteristics performed by one or several units or devices can be performed by any other number of units or devices. For example, steps 102 and 103 can be performed by a single unit or by any other number of different units. The determination, detection, calculation, et cetera steps and/or the control of the fever detection apparatus in accordance with the above described fever detection method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a fever detection apparatus for detecting fever of a living being. A heart rate providing unit provides a heart rate value and a peripheral physiological value providing unit provides a peripheral physiological value, wherein a heart rate characteristics determination unit determines heart rate characteristics from the heart rate value and a peripheral characteristics determination unit determines peripheral characteristics from the peripheral physiological value. A fever detection unit detects fever depending on the heart rate characteristics and the peripheral characteristics. Since the heart rate characteristics and the peripheral characteristics are influenced by fever, the fever detection apparatus can be used to reliably and preferentially unobtrusively detect fever.

The invention claimed is:

1. A fever detection apparatus for detecting fever of a living being, the fever detection apparatus comprising:
 a pulse oximeter configured to measure:
  a plurality of heart rate values being indicative of the heart rate of the living being measured over time, and
  a plurality of peripheral blood perfusion values being indicative of a blood perfusion in the periphery of the living being measured over time,
 at least one processor programmed to:
  determine temporal heart rate characteristics including a temporal pattern from the heart rate values measured over time,
  determine temporal peripheral blood perfusion characteristics including a temporal pattern from the peripheral blood perfusion values measured over time,
  detect a fever of the living being depending on the temporal heart rate characteristics and the temporal peripheral blood perfusion characteristics; and
 a display configured to display an indication of the fever when the fever is detected.

2. The fever detection apparatus as defined in claim 1, wherein the pulse oximeter is further programmed to:
 measure a plurality of skin temperature values being indicative of a skin temperature of the living being; and
 the at least one processor is further programmed to:
  determine a temporal skin temperature pattern from the skin temperature values measured over time; and
  detect a fever of the living being depending on the temporal skin temperature pattern.

3. The fever detection apparatus as defined in claim 1, wherein the at least one processor is further programmed to apply predefined fever detection rules to the temporal heart rate pattern and the peripheral blood perfusion pattern.

4. The fever detection apparatus as defined in claim 3, wherein the fever detection rules are predefined such that fever is detected if the heart rate value increases and the peripheral blood perfusion value decreases in a same time interval.

5. The fever detection apparatus as defined in claim 4, wherein the at least one processor is further programmed to determine a heart rate gradient from the heart rate values measured over time and a peripheral blood perfusion gradient from the peripheral blood perfusion values measured over time.

6. The fever detection apparatus as defined in claim 5, wherein the fever detection rules are predefined such that fever is detected, if the heart rate gradient is positive indicating a heart rate increase and the peripheral blood perfusion gradient is negative indicating an decrease of the peripheral blood perfusion value within a same time interval.

7. The fever detection apparatus as defined in claim 6, wherein the fever detection rules are predefined such that fever is detected if an absolute peripheral blood perfusion gradient is larger than a peripheral threshold and an absolute heart rate gradient is larger than a heart rate threshold.

8. The fever detection apparatus as defined in claim 4, wherein the at least one processor is programmed to:
 measure an initial heart rate value and an actual heart rate value and an initial peripheral blood perfusion value and an actual peripheral blood perfusion value, and determine a heart rate change based on the provided initial and actual heart rates and a peripheral blood perfusion change based on the provided initial and actual peripheral blood perfusion values, wherein the fever detection rules are predefined such that fever is detected, if the heart rate change indicates an increase of the heart rate and the peripheral change indicates a decrease of the peripheral blood perfusion value in a same time interval.

9. The fever detection apparatus as defined in claim wherein the at least one processor is further programmed to apply predefined fever probability rules to the temporal peripheral blood perfusion pattern and the temporal heart rate pattern for determining a fever property value being indicative of the probability of having fever.

10. The fever detection apparatus as defined in claim 1, wherein the at least one processor is further programmed to apply predefined fever recovery rules to the temporal peripheral blood perfusion pattern and the temporal heart rate pattern for detecting recovery from fever, wherein the fever recovery rules being predefined such that recovery from fever is detected, if the peripheral blood perfusion value increases and the heart rate decreases in a same time interval.

11. The fever detection apparatus as defined in claim 1, wherein the fever detection apparatus further comprises a sensor configured to monitor a further measured property of the living being or a property of the surrounding of the living being, the measured property including at least one of ambient temperature, respiratory rate, physical activity type, physical activity level, body posture, body movement, and a position of the pulse oximeter;

wherein, the at least one processor is further programmed to detect fever depending on the peripheral blood perfusion value, the heart rate and the property provided by the sensor.

12. A non-transitory computer readable medium storing instructions for performing a fever detection method for detecting fever of a living being, the fever detection method comprising:

with a pulse oximeter,
measuring a plurality of heart rate values being indicative of the heart rate of the living being measured over time;
measuring a plurality of skin temperature values being indicative of a skin temperature of the living being;
measuring a plurality of peripheral blood perfusion values being indicative of a blood perfusion in the periphery of the living being measured over time;

with at least one processor,
determining a temporal heart rate pattern from the heart rate values measured over time;
determining a temporal skin temperature pattern from the skin temperature values measured over time;
determining a temporal blood perfusion pattern from the peripheral blood perfusion values measured over time; and
detecting a fever of the living being depending on the temporal heart rate pattern, the temporal skin temperature pattern and the temporal blood perfusion pattern based on at least one when the heart rate value increases and the peripheral blood perfusion value decreases in a same time interval; and
detecting recovery from fever when the peripheral blood perfusion value increases and the heart rate decreases in a same time interval.

13. A fever detection apparatus for detecting fever of a living being, the fever detection apparatus comprising:
a pulse oximeter configured to measure a plurality of heart rate values being indicative of the heart rate of the living being measured over time a plurality of peripheral blood perfusion values being indicative of the peripheral blood perfusion of the living being measured over time and a plurality of skin temperature values being indicative of a skin temperature of the living being measured over time;
at least one processor programmed to:
measure heart rate values over time;
determine a temporal heart rate gradient of the heart rate values measured over time;
measure peripheral blood perfusion values over time;
determine a temporal peripheral blood perfusion pattern from the peripheral blood perfusion value measured over time;
measure skin temperature values over time;
determine a temporal skin temperature gradient of the skin temperature values measured over time; and
apply predefined fever detection rules to the temporal heart rate gradient, the temporal peripheral blood perfusion pattern, the temporal skin temperature gradient to detect a fever of the living being; and
a display configured to display an indication of the fever when the fever is detected.

14. The fever detection apparatus as defined in claim 13, wherein the fever detection rules are predefined such that fever is detected, if the heart rate gradient is positive indicating a heart rate increase and the skin temperature gradient is negative indicating a decrease of the skin temperature within a same time interval.

15. The fever detection apparatus as defined in claim 14, wherein the fever detection rules are predefined such that fever is detected, if an absolute peripheral skin temperature gradient is larger than a skin temperature threshold and an absolute heart rate gradient is larger than a heart rate threshold.

16. The fever detection apparatus as defined in claim 13, wherein the at least one processor is further programmed to:
measure an initial heart rate value and an actual heart rate value, and an initial skin temperature value and an actual skin temperature value, and
determine a heart rate change based on the provided initial and actual heart rates and a skin temperature change based on the provided initial and actual skin temperature values,
wherein the fever detection rules are predefined such that fever is detected, if the heart rate change indicates an increase of the heart rate and the skin temperature change indicates a decrease of the skin temperature value in a same time interval.

17. The fever detection apparatus as defined in claim 13, wherein the at least one processor is further programmed to apply predefined fever probability rules to the skin temperature gradient and the heart rate gradient for determining a fever property value being indicative of the probability of having fever.

18. The fever detection apparatus as defined in claim 13, wherein the at least one processor is further programmed to apply predefined fever recovery rules to the skin temperature gradient and the heart rate gradient for detecting recovery from fever, the fever recovery rules being predefined such that recovery from fever is detected if the skin temperature value increases and the heart rate decreases in a same time interval.

19. The fever detection apparatus as defined in claim 13, wherein the fever detection apparatus further comprises a sensor configured to monitor at least one property of ambient temperature, respiratory rate, physical activity type, physical activity level, body posture, body movement, and a position of the pulse oximeter; and the at least one processor is further programmed to detect fever depending on the skin temperature value, the heart rate and the property monitored by the sensor.

* * * * *